United States Patent [19]

Kleemann et al.

[11] 4,322,552

[45] Mar. 30, 1982

[54] PROCESS FOR THE PRODUCTION OF 4-AMINOBUTYRAMIDE HYDROCHLORIDE

[75] Inventors: Axel Kleemann, Hanau; Jurgen Martens, Alzenau; Horst Weigel, Rodenbach, all of Fed. Rep. of Germany

[73] Assignee: Degussa Aktiengesellschaft, Frankfurt, Fed. Rep. of Germany

[21] Appl. No.: 208,022

[22] Filed: Nov. 18, 1980

[30] Foreign Application Priority Data

Nov. 28, 1979 [DE]  Fed. Rep. of Germany ........ 2947825

[51] Int. Cl.$^3$ .......................................... C07C 102/00
[52] U.S. Cl. .................................... 564/198; 564/124
[58] Field of Search ................ 564/198, 490, 124, 493

[56] References Cited

U.S. PATENT DOCUMENTS

| | | | |
|---|---|---|---|
| 3,117,162 | 1/1964 | Rylander et al. | 564/490 |
| 4,003,933 | 1/1977 | Drake | 564/493 |
| 4,137,267 | 1/1979 | Reid et al. | 564/490 |

OTHER PUBLICATIONS

Wagner et al., Synthetic Organic Chemistry, John Wiley & Sons, N.Y., N.Y., 1955, p. 660.

*Primary Examiner*—Arthur P. Demers
*Attorney, Agent, or Firm*—Cushman, Darby & Cushman

[57] ABSTRACT

4-aminobutyramide hydrochloride is produced by hydrogenation of 3-cyanopropionamide in the presence of a solvent inert under the reaction conditions, a noble metal catalyst and hydrogen chloride at a temperature between 5° and 80° C. The hydrochloride can be easily converted into 4-aminobutyramide which as such or in the form of derivatives has significance as a neurotransmitter.

16 Claims, No Drawings

PROCESS FOR THE PRODUCTION OF 4-AMINOBUTYRAMIDE HYDROCHLORIDE

SUMMARY OF THE INVENTION 4-aminobutyramide and derivatives thereof have significance as therapeutics, particularly as neurotransmitters.

The object of the invention is the development of a process for the production of 4-aminobutyramide hydrochloride which is characterized by hydrogenating 3-cyanopropionamide in the presence of a solvent inert under the conditions of the reaction, a noble metal catalyst and hydrogen chloride at a temperature between 5° and 80° C.

The process of the invention makes possible the production of 4-aminobutyramide monohydrochloride in a very simple manner, which hydrochloride then in a likewise very simple manner, e.g. by treatment with a basic ion exchanger or with a suitable base, can be converted into the 4-aminobutyramide.

The 3-cyanopropionamide serving as starting material can be produced for example by partial saponification of succinodinitrile. Hydrogenation of the 3-cyanopropionamide takes place in the presence of a solvent inert under the conditions of the hydrogenation reaction. Suitable solvents are monohydric or dihydric alcohols having 2 to 6, preferably 2 to 3 carbon atoms or their mixtures with water, as well as mixtures of cyclic ethers having 4 to 10 carbon atoms, particularly tetrahydrofuran or 1,4-dioxane with water. Illustrative of suitable alcohols are ethanol, propanol, isopropanol, butanol, pentanol, butanol-2, 2-methyl propanol, hexanol, ethylene glycol, propylene glycol, trimethylene glycol, tetramethylene glycol and hexamethylene glycol. The amount of solvent employed is not critical, however, it should be suitably so regulated that the 3-cyanopropionamide employed is completely soluble at the reaction temperature chosen. Particularly preferred solvents are straight or branched chain alkanols having 2 to 6 carbon atoms, particularly ethanol.

The hydrogenation furthermore requires the presence of a noble metal catalyst, particularly a platinum metal catalyst. Especially preferred catalysts are metallic rhodium or platinum and platinum IV oxide. There can also be employed just as well mixtures of several noble metals or mixtures of noble metals with platinum IV oxide. Other noble metal catalysts include for example palladium, ruthenium and rhenium. The catalysts can be used in the free form or on carriers (e.g. precipitated on activated carbon). They can be recovered after the end of the hydrogenation and be employed again without further purification, whereby in the case of platinum IV oxide, it is unimportant whether after the first use it is present partially or completely reduced to $Pt^{2+}$ compounds or metallic platinum. The amount of noble metal catalyst added is not critical. For attaining short hydrogenation times, however, it is recommended that the noble metal catalyst be employed in an amount of 1 to 20, preferably 5 to 10, weight percent based on the 3-cyanopropionamide employed.

The hydrogenation of the 3-cyanopropionamide takes place finally in the presence of hydrogen chloride which suitably is used in equimolar amount to the 3-cyanopropionamide employed. However, it is also possible to use a slight excess of hydrogen chloride.

The hydrogenation takes place at a temperature between 5° and 80° C., preferably between 25° and 50° C. It can be undertaken without the use of super atmospheric pressure by leading hydrogen through the reaction mixture or by the use of a hydrogen pressure up to 100 bar in a pressure resistant reaction vessel. Preferably the hydrogenation takes place at pressures up to 5 bar. The hydrogen pressure to be sure has a certain influence on the time required for the complete hydrogenation, which is somewhat shortened with increasing pressure, but hardly on the purity of the 4-aminobutyramide hydrochloride formed.

If the hydrogenation is carried out in a straight or branch chain alkanol having 2 to 6, preferably 2 or 3 carbon atoms, then the 4-aminobutyramide hydrochloride separates out in crystalline form during the hydrogenation or, if this is carried out at higher temperature, after the cooling of the reaction mixture to room temperature, then it can be filtered off together with the catalyst. The 4-aminobutyramide hydrochloride can then be brought into solution by digesting the filter cake witth warm methanol and separated off from the catalyst by decantation or filtration.

Unless otherwise indicated all parts and percentages are by weight.

The process can comprise, consist essentially of or consist of the stated steps with the materials recited.

The invention is further explained in connection with the following examples.

DETAILED DESCRIPTION

EXAMPLE 1

Hydrogen gas was led under normal (atmospheric) pressure at 30° to 35° C. through a reaction mixture made of 9.8 grams (0.1 mole) of 3-cyanopropionamide, 3.65 grams (0.1 mole) of hydrogen chloride, 0.75 grams of platinum IV oxide and 150 ml of ethyl alcohol. After the end of the uptake of hydrogen the 4-aminobutyramide, crystallized out, together with the catalyst, was filtered off. The filter cake was treated with warm methanol whereby the 4-aminobutyramide went into solution. This methanolic solution was filtered, concentrated and cooled whereby the 4-aminobutyramide hydrochloride again crystallized. Yield: 11.5 grams (83% theory). Melting Point: 134°–137° C.

$^1$H-NMR(DMSO-d$_6$+CDCl$_3$): δs8.25(Δ—NH$_3$·3H),

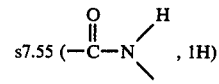

s7.55 (1H)

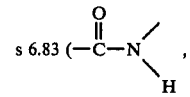

s 6.83 (1H), m2.83 (CH$_2$, 2H), m2.22 (CH$_2$, 2H) and m1.9 (CH$_2$, 2H) ppm.

EXAMPLE 2

Example 1 was repeated with the sole difference that in place of the platinum IV oxide there was employed 0.75 grams of metallic platinum as catalyst. Yield: 60% of theory. Melting Point: 134°–136° C.

EXAMPLE 3

Example 1 was repeated with the sole difference that in place of ethanol there were employed 150 ml of isopropyl alcohol as solvent. Yield: 38% of theory. Melting Point: 134°–136° C.

EXAMPLE 4

Example 1 was repeated with the sole difference that in place of ethanol there were employed 150 ml of n-butanol as solvent. Yield: 39% of theory. Melting Point: 134°–136° C.

EXAMPLE 5

Example 1 was repeated with the sole difference that the hydrogenation was undertaken in a shaking autoclave at a hydrogen pressure of 5 bar. Yield: 84% of theory. Melting Point: 135°–137° C.

EXAMPLE 6

Example 1 was repeated with the sole difference that the hydrogenation was carried out in the presence of 0.8 grams of rhodium in place of the platinum IV oxide. Yield: 63% of theory. Melting Point: 136°–138° C.

The entire disclosure of German priority application No. P 2947825.9-42 is hereby incorporated by reference.

What is claimed is:

1. A process for the production of 4-aminobutyramide hydrochloride comprising hydrogenating 3-cyanopropionamide in the presence of a solvent inert under the reaction conditions, a noble metal catalyst and hydrogen chloride at a temperature between 5° and 80° C.

2. The process of claim 1 wherein the inert solvent is an alkanol having 2 to 6 carbon atoms.

3. The process of claim 2 wherein the alkanol has 2 to 3 carbon atoms.

4. The process of claim 3 wherein the alkanol is ethanol.

5. The process of claim 2 wherein the hydrogenation is carried out at a pressure between atmospheric pressure and 100 bar.

6. The process of claim 1 wherein the hydrogenation is carried out at a pressure between atmospheric pressure and 100 bar.

7. The process of claim 6 wherein the noble metal catalyst is metallic platinum, platinum IV oxide or a mixture of platinum and platinum IV oxide.

8. The process of claim 5 wherein the noble metal catalyst is metallic platinum, platinum IV oxide or a mixture of platinum and platinum IV oxide.

9. The process of claim 2 wherein the hydrogenation is carried out at a pressure between atmospheric pressure and 100 bar.

10. The process of claim 1 wherein the hydrogenation is carried out at a pressure between atmospheric pressure and 100 bar.

11. The process of claim 1 wherein the noble metal catalyst is rhodium, platinum or platinum IV oxide or mixtures thereof.

12. The process of claim 11 wherein the solvent is a monohydric or dihydric alcohol having 2 to 6 carbon atoms or a cyclic ether having 4 to 10 carbon atoms or a mixture of such alcohol or cyclic ether with water.

13. The process of claim 12 wherein the solvent is (a) an alkanol having 2 to 6 carbon atoms, (b) tetrahydrofuran, (c) 1,4-dioxane or (d) a mixture of (a), (b) or (c) with water.

14. The process of claim 13 wherein the noble metal catalyst is used in an amount of 1 to 20 weight percent, based on the 3-cyanopropionamide.

15. A process according to claim 1 wherein the noble metal catalyst is the sole catalyst.

16. A process according to claim 1 wherein the process consists essentially of hydrogenating 3-cyanopropionamide in the presence of a solvent inert under the reaction conditions, a noble metal catalyst and hydrogen chloride at a temperature between 5° and 80° C.

* * * * *